United States Patent
Fine et al.

(10) Patent No.: US 10,113,983 B1
(45) Date of Patent: Oct. 30, 2018

(54) EXPLOSIVES VAPOR DETECTOR

(75) Inventors: David H. Fine, Sudbury, MA (US); Freeman W. Fraim, Lexington, MA (US); James E. Buckley, Bedford, MA (US)

(73) Assignee: THERMO FISHER SCIENTIFIC INC., San Jose, CA (US)

( * ) Notice: Subject to any disclaimer, the term of this patent is extended or adjusted under 35 U.S.C. 154(b) by 0 days.

(21) Appl. No.: 06/732,449

(22) Filed: May 9, 1985

(51) Int. Cl.
  *G01N 1/02* (2006.01)
  *G01N 24/08* (2006.01)

(52) U.S. Cl.
  CPC ............ *G01N 24/084* (2013.01); *G01N 1/02* (2013.01)

(58) Field of Classification Search
  CPC .............................. G01N 1/02; G01N 24/084
  USPC ....... 436/166, 199, 157, 178, 181, 198, 106; 436/156, 159, 160, 161; 422/88, 94, 163; 55/28, 208
  See application file for complete search history.

(56) References Cited

U.S. PATENT DOCUMENTS

| | | | |
|---|---|---|---|
| 2,373,113 A * | 4/1945 | Francis | 422/88 |
| 3,430,482 A | 3/1969 | Dravniek et al. | 73/23.1 |
| 3,568,411 A | 3/1971 | Dravniek et al. | 55/208 |
| 3,701,632 A | 10/1972 | Lovelock | 23/232 E |
| 3,864,451 A * | 2/1975 | Lee et al. | 423/244 |
| 3,919,397 A * | 11/1975 | Gould | 436/116 |
| 3,942,357 A | 3/1976 | Jenkins | 73/23 |
| 3,973,910 A | 8/1976 | Fine | 23/230 PC |
| 3,996,003 A | 12/1976 | Fine et al. | 23/230 PC |
| 3,996,009 A | 12/1976 | Fine et al. | 23/254 R |
| 3,998,101 A | 12/1976 | Bradshaw et al. | 73/421.5 R |
| 4,023,929 A * | 5/1977 | Becker et al. | 436/158 |
| 4,045,997 A | 9/1977 | Showalter et al. | 73/23 |
| 4,166,379 A | 9/1979 | Bradshaw | 73/29 |

(Continued)

FOREIGN PATENT DOCUMENTS

| | | | | |
|---|---|---|---|---|
| JP | 0146273 | * | 11/1979 | 55/208 |
| WO | 8301512 | * | 4/1983 | 422/89 |

OTHER PUBLICATIONS

Lafleur et al., *Anal. Chem.*, vol. 53, 1981 pp. 1202-1205.*

(Continued)

*Primary Examiner* — Marshall P O'Connor
(74) *Attorney, Agent, or Firm* — Herbert E. Messenger

(57) ABSTRACT

Disclosed are a highly selective, highly sensitive method and apparatus for detecting vapors from explosives at low concentrations such as 1 part in $10^{14}$. Airborne explosives vapors are selectively adsorbed on a spiral-wound platinum or platinum-coated ribbon of a preconcentrator cartridge while trapping of nitrogen oxides is avoided. The vapors are released and partially decomposed to liberate nitric oxide gas by flash-heating of the ribbon, these products may then be pyrolyzed if necessary to complete the liberation of nitric oxide gas, and then the liberated nitric oxide gas is detected, as by chemiluminescent detection. Also described are various systems incorporating the explosives vapor detector such as a walk-through portal, a vehicle sniffer, and a system incorporated into the air-handling apparatus of a building. A walk-through explosives detection system is disclosed having a carousel containing an array of preconcentrator cartridges for rapid acquisition and analysis of explosives vapor samples, and which is capable of screening up to ten persons per minute for possession of explosives.

10 Claims, 10 Drawing Sheets

(56) References Cited

U.S. PATENT DOCUMENTS

| | | | | |
|---|---|---|---|---|
| 4,202,200 A | | 5/1980 | Ellson | 73/23 |
| 4,293,316 A | | 10/1981 | Block | 55/16 |
| 4,301,114 A | | 11/1981 | Rounbehler et al. | 422/5 |
| 4,329,487 A | * | 5/1982 | Orito et al. | 502/167 |
| 4,409,006 A | * | 10/1983 | Mattia | 55/28 |

OTHER PUBLICATIONS

Bender, E.C. "Analysis of Smokeless Powders Using UV/TEA Detection" *Proceedings of the International Symposium on the Analysis and Detection of Explosives*, Mar. 29, 1983.

Fine, D.H. et al, Picogram Analyses of Exposive Residues Using the the Thermal Energy Analyzer (TEA), *Journal of Forensic Science*, Jul. 1984.

Spangler, G.E., "Comments on the Potential Use of $NO_x$ Chemiluminescence for TNT Detection", USAMERDC Technical Note 1974 (Unpublished).

\* cited by examiner

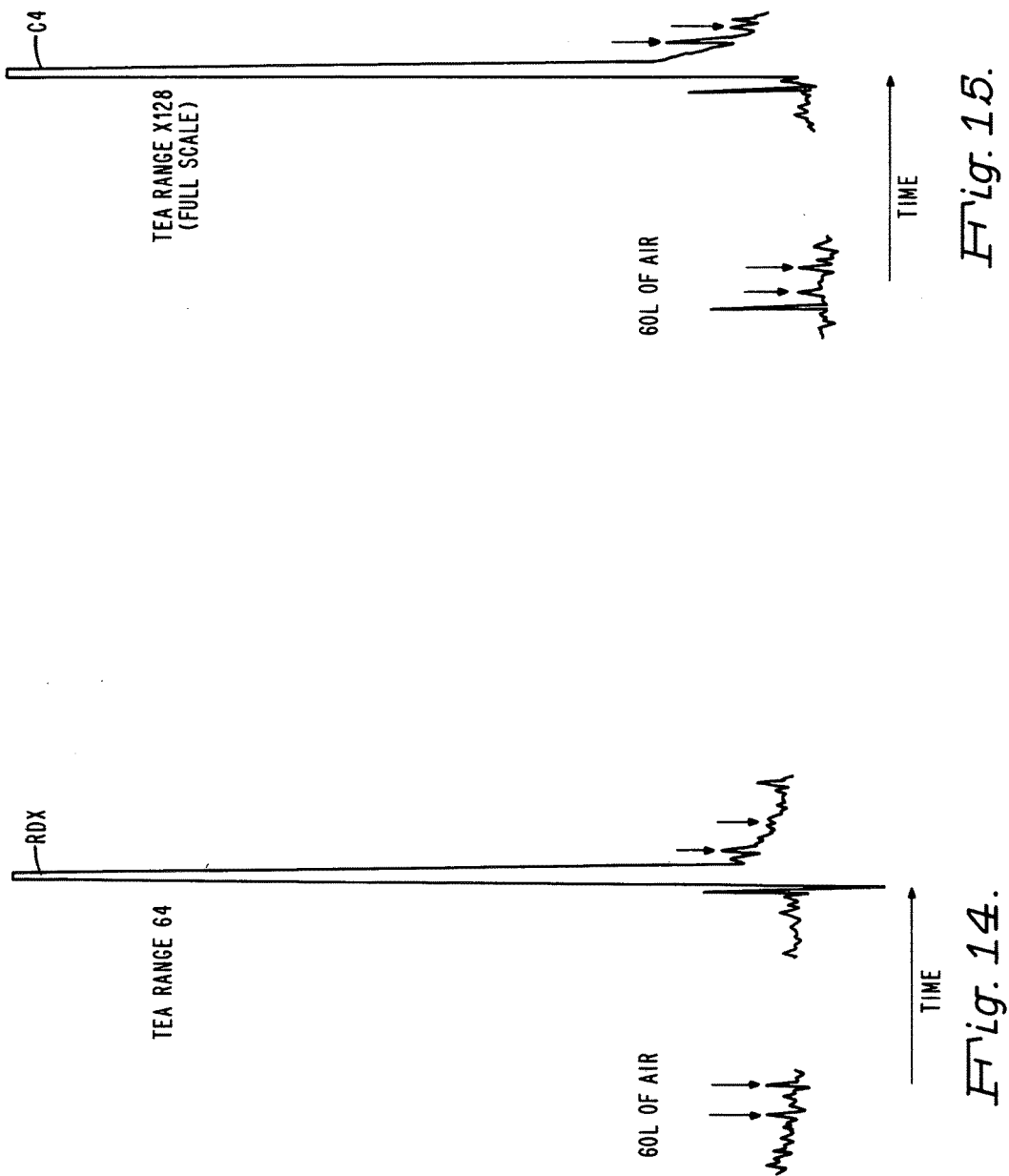

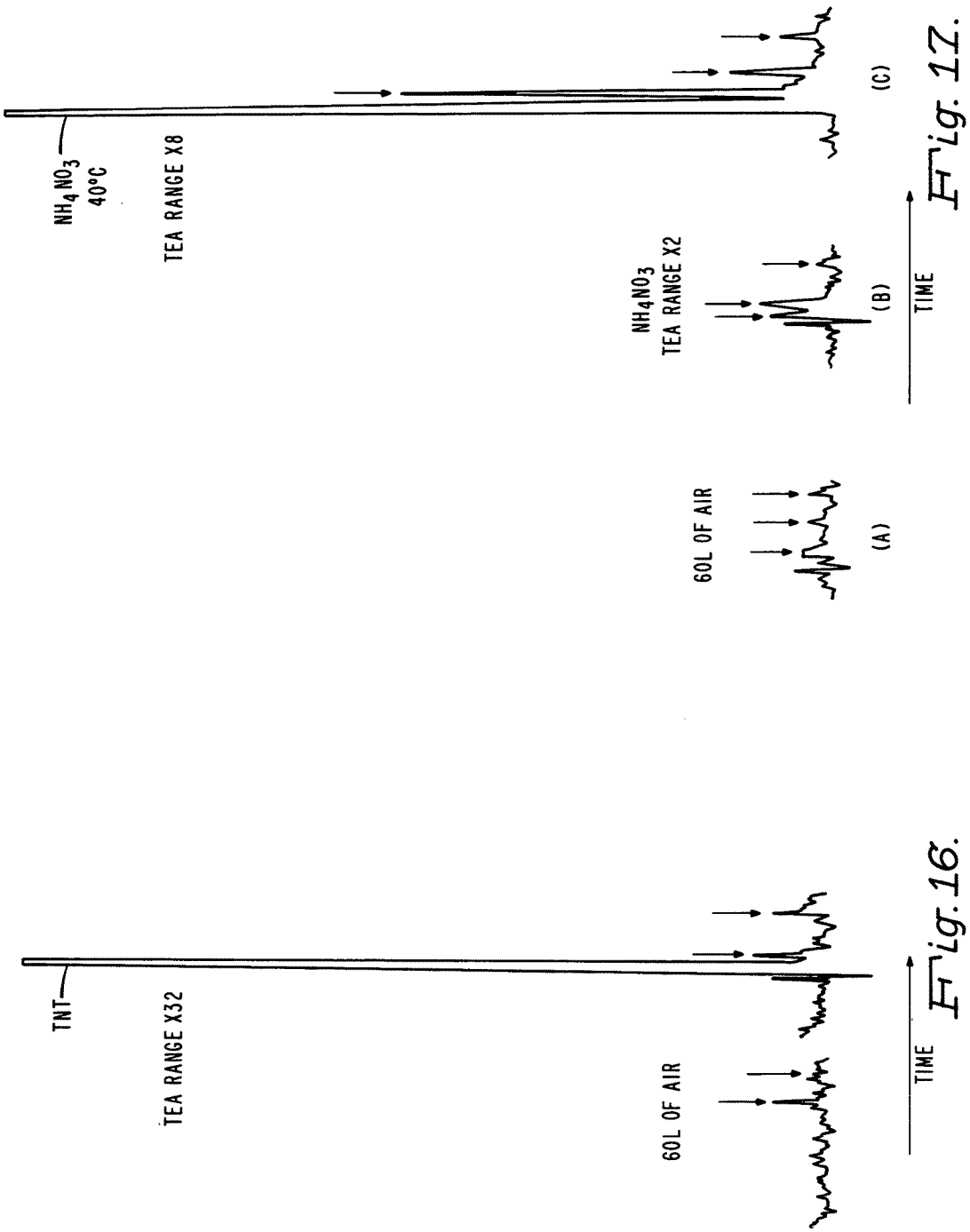

EXPLOSIVES VAPOR DETECTOR

The Government has rights in this invention pursuant to Contract No. DTRS-57-84-000063 awarded by U.S. Department of Transportation.

BACKGROUND OF THE INVENTION

This invention relates to detection of explosives and in particular to the selective detection of very small amounts of vapors emanating from explosives.

Detection of explosives carried by persons or located in buildings, cars, or packages can be important to the protection of people and property. For example, it is essential that terrorists with bombs be intercepted prior to boarding commercial airplanes or entering buildings, and it is also desirable to be able to "sniff" buildings and vehicles to determine whether they contain explosives. To be effective, a detection system employed in screening persons for possible possession of explosives should be rapid, reliable have high selectivity and sensitivity, and be as non-intrusive as possible. In applications such as the searching of rooms or buildings or in screening vehicles other important characteristics of a detection system may include portability, ruggedness, and an ability to function in harsh environments.

Various techniques have been employed in detection of explosives. For example, nitric oxide-chemiluminescence technology has been used for analysis of explosive residues at the picogram level, but such systems included gas chromatographs or liquid chromatographs not useful in real time detection of explosives vapors. Electron capture detectors have been used commercially to detect dynamite, but have proven unable to achieve the high sensitivities (e.g. one part in $10^{14}$) needed for detection of certain explosives having very low vapor pressures. This limitation is due mainly to a lack of selectivity, i.e., the electron capture devices respond not only to explosives vapors, but also to substances such as oxygen, nitrogen oxides, halogenated solvents, water vapor, and phthalates which are present in excess amounts in the background. Dogs have been used effectively in certain circumstances but lack the sensitivity to consistently detect certain explosives such as RDX, PETN, and the water gels. Mass spectrometry and ion mobility spectroscopy have been shown to be highly sensitive to electronegative compounds including explosives; however, this high sensitivity has come at the expense of a loss of selectivity. If other electronegative species such as halogenated solvents, water vapors, and phthalates are present along with vapors of explosives, these species compete for detection and overload or reduce the effective sensitivity of mass spectrometers and ion mobility spectroscopes.

Accordingly, it is an object of the invention to provide an improved method and apparatus for detecting vapors from explosives.

It is an object of the invention to provide an explosives vapor detector capable of detecting explosives vapors essentially in real time at concentrations of as low as one part in $10^{14}$ or less.

It is an object of the invention to provide an explosives vapor detector which is highly sensitive to vapors of explosives but does not respond to substances which would interfere with detection of explosives.

It is an object of the invention to provide a highly sensitive, highly selective explosives vapor detector capable of achieving large sample preconcentrations without large pressure drops.

It is an object of the invention to provide systems incorporating a highly sensitive, highly selective explosives vapor detector which are capable of rapidly screening a succession of persons or articles for the presence of explosives.

It is an object of the invention to provide systems incorporating a highly sensitive, highly selective explosives vapor detector which may be used to screen vehicles or to search or monitor areas of buildings for the presence of explosives.

It is an object of the invention to provide a walk-through explosives vapor detection system which is rapid, effective, and of minimal intrusiveness to persons being screened.

It is an object of the invention to provide a microprocessor-controlled explosives vapor detection system whose sensitivity can readily be varied.

SUMMARY OF THE INVENTION

The invention is a highly selective, highly sensitive method and apparatus for detecting explosives by trapping, decomposing, and analyzing of their airborne vapors. The method attains high selectivity through techniques and components which avoid trapping of potential interferents such as nitrogen oxides, through selective removal of any interferents trapped, and through analysis highly specific to compounds whose thermal decomposition produces nitric oxide (NO). According to the invention airborne explosives vapors at concentrations as low as several parts in $10^{16}$ are selectively collected on surfaces of a trapping medium such as a platinum or platinum-coated metal ribbon. After a desired time interval of collection, gases and trapped $NO_x$ are removed from the preconcentrator by application of vacuum and moderate heating of the ribbon, and then the ribbon is flash-heated. Flash-heating releases the concentrated explosives vapors from the ribbon and partially decomposes the vapors of certain explosives to form NO gas. The vapors are directed into a nitric oxide detector or; if necessary, first into a pyrolyzer to liberate NO gas from any explosives vapors not thermally decomposed during flash-heating. The NO is then detected, as by chemiluminescent reaction of NO with ozone, by photoionization, or any other suitable NO detection technique, and the detection of NO confirms the presence of explosives.

In a preferred embodiment of the invention the explosives vapors detector includes several cartridge-shaped preconcentrators held in a carousel. Rotation either of the carousel or of flow connections adjacent to the inlet and outlet of the carousel successively positions each preconcentrator at stations at which various steps of explosives detection are performed. In a detection cycle an air sample which may contain explosives vapors is first drawn through a preconcentrator and explosives vapors are selectively trapped on the platinum surface of a spiral-shaped platinum-coated metal ribbon. After a predetermined time interval this preconcentrator is rotated (if in a rotatable carousel) into alignment with a second station and a second preconcentrator is positioned for collection of explosive vapors. The preconcentrator at the second station is moderately heated, for example, to a temperature of about 150° C. and degassed under vacuum. After being moved again to a third station, the platinum-coated ribbon of the degassed preconcentrator is flash-heated to red heat (e.g., to about 800° C.). Flash-heating releases and partially decomposes the explosives vapors, which are then directed to a pyrolyzer which may also be operated at a temperature of about 800° C. In the pyrolyzer the sample vapors are further decomposed to release NO gas. The ND gas then passes to a chamber of a chemiluminescent detector where it is reacted with ozone, and the chemiluminescent radiation emitted at selected wavelengths by the reaction is monitored by infrared detection such as by a photomultiplier tube, producing a signal indicating the presence of explosives vapors. Thereafter, the preconcentrator from which sample vapors have been removed is successively positioned at cleaning and cooldown stations in preparation for another detection cycle. Cleaning of the preconcentrator preferably includes reheating of the collection ribbon to burn off any deposits of carbon or other contaminants.

The explosives detector may, in accordance with the invention, be incorporated into any of various systems such as a walk-through portal, a vehicle sniffer, and fixed and portable systems for monitoring areas of buildings and other locations. The walk-through portal explosives detection system includes an enclosed test chamber in which persons may be screened individually at a rate of up to about ten persons per minute for the presence of explosives. A preferred walk-through system includes a carousel of preconcentrators mounted adjacent to the test chamber and a blower and fans for directing airflow through the chamber to sweep vapors from a person to be screened. A sample analyzer is positioned in close proximity to the carousel, and system operation is controlled by a microprocessor.

BRIEF DESCRIPTION OF THE DRAWINGS

FIGS. 14-17 are timewise signal traces of the output of the experimental detector illustrated in FIGS. 9 and 10.

DESCRIPTION OF PREFERRED EMBODIMENTS

In the method and apparatus of the invention the presence of explosives is determined through detection of small amounts of vapor given off by the explosives. Examples of explosives which can be detected at concentrations as low as one part in $10^{14}$, and possibly as low as several parts in $10^{16}$, include trinitrotoluene (TNT), dinitrotoluene (DNT), pentaerythritol tetranitrate (PETN), ethylene glycol dinitrate (EGDN), nitroglycerin (NG), cyclo 1, 3, 5-trimethylene-2, 4, 6-trinitramine (RDX), cyclotetramethylene tetranitramine (HMX), and water gels (composed primarily of ammonium nitrate, sensitized with various additives). A distinguishing characteristic of most of these explosives is the nitro ($-NO_2$) functional group, typically attached to a carbon, nitrogen, or oxygen atom. The method of the invention provides a technique for selectively collecting explosives vapors and removing potential interferences, releasing and thermally fracturing and decomposing the collected vapors to produce $NO_2$ and then NO, and then selectively detecting the NO.

Figure 1:
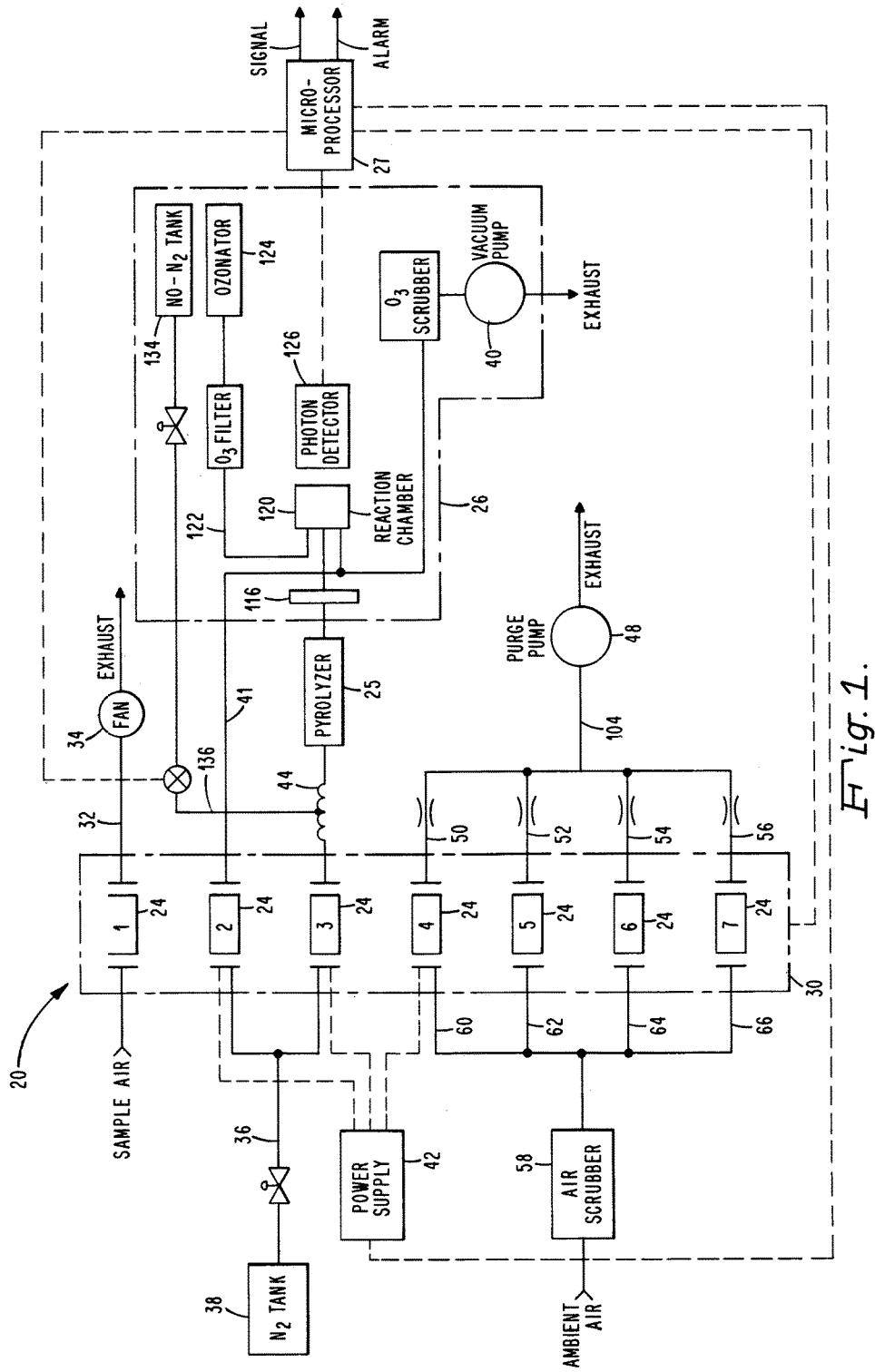
FIG. 1 is a schematic diagram of an explosives vapor detector according to a preferred embodiment of the invention.

As shown in the schematic of FIG. 1, a preferred apparatus 20 for detecting vapors from explosives according to the invention comprises one or more sample preconcentrators 24 positionable at various stations, one of which is connected to a pyrolyzer 25. The pyrolyzer 25 communicates with (or in certain preferred embodiments forms part of) a sample analyzer 26, which in turn may be connected to a microprocessor 27 controlling operation of the explosives vapor detector 20.

It should be understood that although a pyrolyzer is included in the detector 20 of FIG. 1, it is considered within the scope of the invention that thermal decomposition of collected explosives vapors to produce NO gas be completed during flash-heating of the preconcentrator 24 (as described hereinafter). Flash-heating, when controlled to heat the collected vapors to decomposition temperatures during their residence in the preconcentrator, avoids the need for a pyrolyzer. In such embodiments a preconcentrator 24 is connected directly to a suitable NO analyzer 26.

The preconcentrators 24, seven being illustrated in FIG. 1 by way of example, preferably are held in a carousel 30. As set forth in more detail hereinafter, each preconcentrator 24 may be successively aligned with input and output lines associated with a number of stations or positions equal to the number of preconcentrators. Relative movement of the preconcentrators 24 from station to station is achieved by rotation either of the carousel 30 or of system components containing those input and output lines, under control of the microprocessor 27. The use of multiple preconcentrators, with design features as disclosed herein; facilitates rapid sampling and analysis of explosives vapors—i.e., essentially "real-time" detection—such as is needed in screening a group of persons passing one-by-one through a detection system in which the detector 20 is installed.

Figure 2:
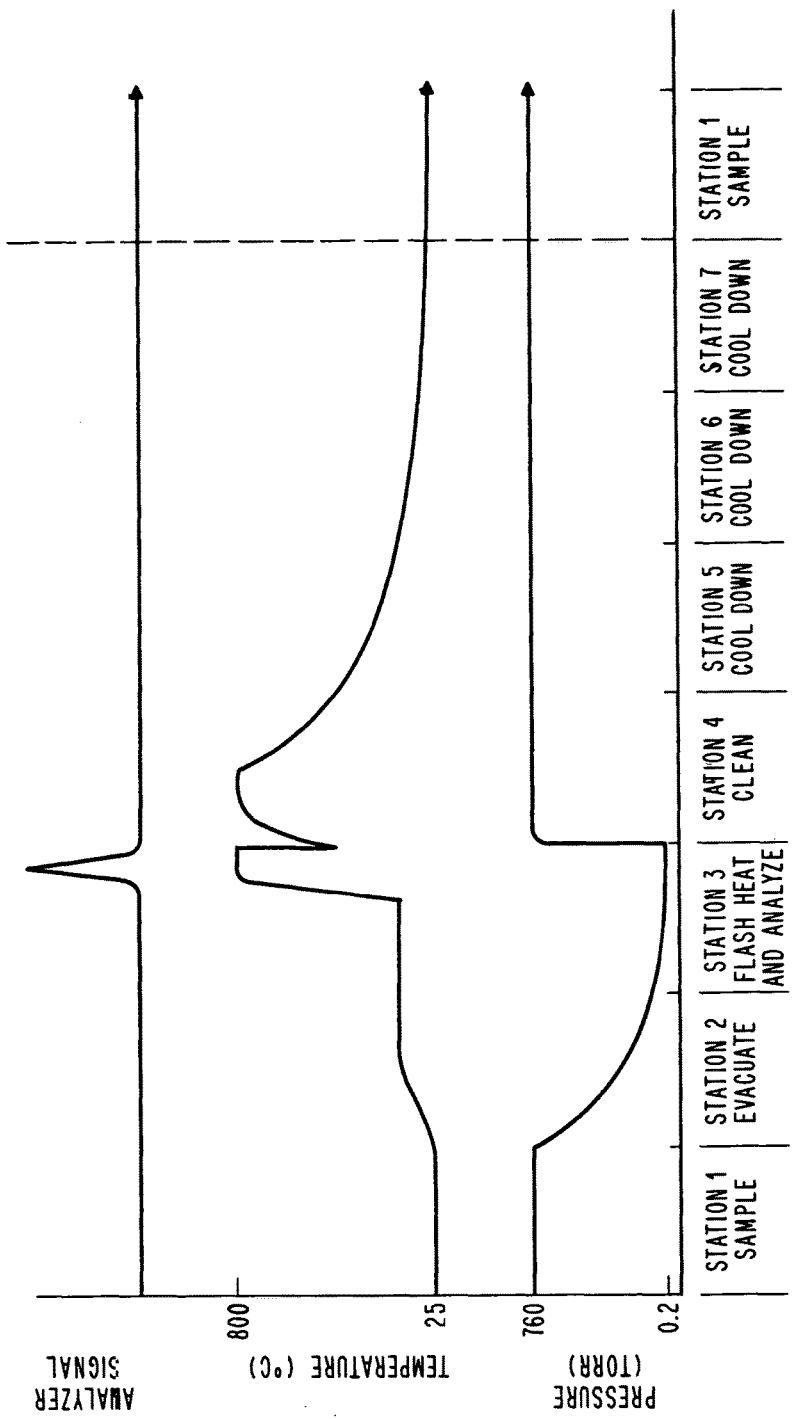
FIG. 2 is a diagram of pressure, temperature, and signal response profiles for seven operating stations of a preferred explosives vapor detector.

Before certain components of the detector are described in more detail, an explanation will be provided of the functions performed at each station with which a preconcentrator 24 may be aligned during a detection cycle. The seven stations and their functions are listed in Table 1, and FIG. 2 shows typical temperature, pressure, and signal profiles associated with each station. For convenience of reference, each of the preconcentrators 24 shown in FIG. 1 is labeled with the number of station at which it is then aligned. It should be noted in connection with these stations and their functions that the carousel 30 holding the preconcentrators 24 is symmetrical and that each preconcentrator preferably spends the same interval of time—e.g., six seconds—at each station.

TABLE 1

Detector Functions

| Station No. | Function |
| --- | --- |
| 1 | Sample |
| 2 | Evacuate |
| 3 | Flash Heat and Analyze |
| 4 | Clean |
| 5-7 | Cool |

At station 1, a preconcentrator 24 held within the carousel 30 is aligned with a sample flow line 32 connected to a fan 34. The fan 34 is operable to rapidly draw a vapor sample through the preconcentrator so that explosives vapors may be selectively trapped and concentrated in a collection medium within the preconcentrator 24.

The purpose of station 2 of the detector 20 is to permit evacuation of gases from a preconcentrator prior to removal of its collected vapors for analysis. At station 2 the carousel 30 is aligned with an input flow line 36 connected to a supply 38 of an inert carrier gas such as nitrogen used to flush out the air space within a preconcentrator. A high speed vacuum pump 40 connected to station 2 of the carousel 30 through an outlet line 41 assists in rapid evacuation of the preconcentrator. The vacuum pump 40 may, as shown in FIG. 1, form part of and provide vacuum pumping for, the sample analyzer 26.

During evacuation the preconcentrator at station 2 preferably is also heated to a temperature in the range of about 25° C.-230° C., typically to about 150° C. by a suitable heater such as a power supply 42 electrically connected to stations 2-4 of the carousel 30 and whose operation is controlled by the microprocessor 27. This heating drives off any nitrogen oxides ($NO_x$) which may be trapped in the preconcentrator 24 without driving off the trapped explosives vapors.

After being evacuated at station 2, a preconcentrator is positioned at station 3 where evacuation may continue for a brief time interval, after which a vapor sample is removed from the preconcentrator and directed along a heated interface or flow line 44 to the pyrolyzer 25 and then to the vapor analyzer 26 for analysis. Removal is effected by flash-heating the vapor collection medium of the preconcentrator to a temperature in the range of about 600° C.-900° C., typically about 800° C., preferably by means of the variable, high-current, low voltage power supply 42 which contains, or is connected to, electronic timing circuitry so as to provide reproducible heating pulses. Carrier gas (e.g., nitrogen) fed to the preconcentrator along inlet line 46, combined with low pressures produced by a vacuum pump such as the pump 40, drive the flash-heated, partially decomposed explosives vapors to the pyrolyzer 25 for completion of the decomposition into NO gas and other fragments.

Figure 5:
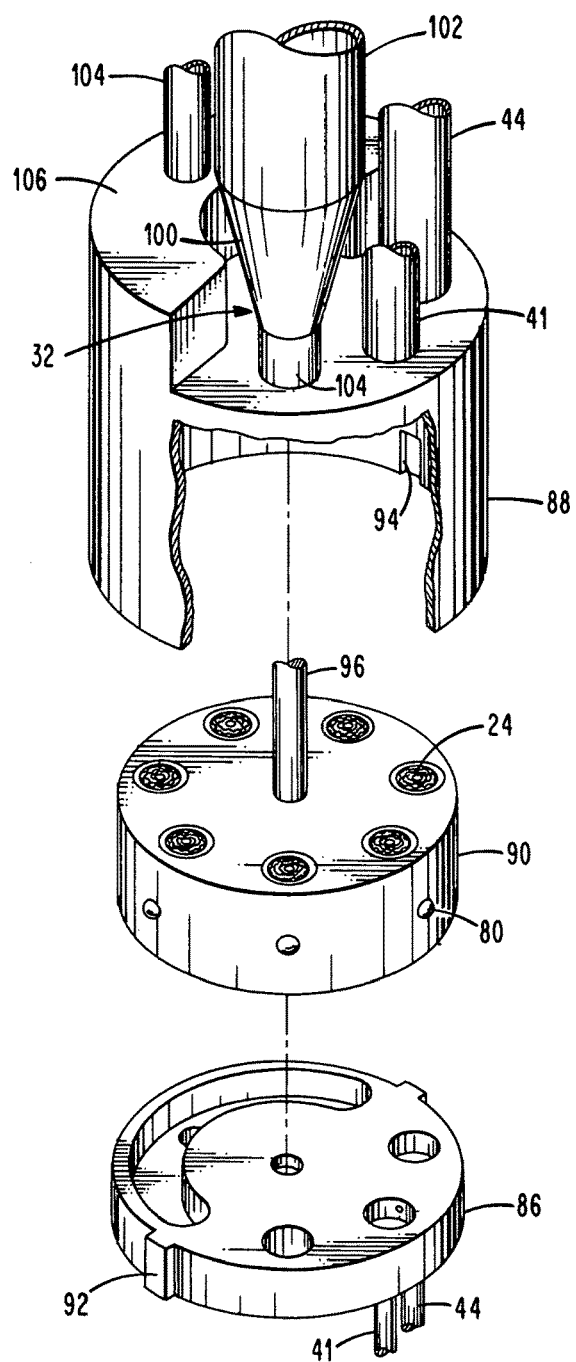
FIG. 5 is an exploded view of a carousel for use in holding sample preconcentrators of the explosives vapor detector of FIG. 1.

At the remaining stations (4-7) to which a preconcentrator is moved during a detection cycle, the preconcentrator is cleaned and cooled by ambient air drawn through it by a purge pump 48 connected to these carousel stations along flow line 50, 52, 54, and 56, respectively (these individual flow lines may be combined into a single manifold as illustrated in FIG. 5). Preferably the ambient air is passed through a scrubber 58 prior to flowing to a manifold (not shown) or along individual lines 60, 62, 64, and 66 to stations 4-7. During cleaning at station 4 the vapor collection medium of the preconcentrator is heated by the power supply 42 to a temperature of about 800° C. to burn off any absorbed carbonaceous material (e.g. dust, tobacco, smoke, or bacteria) or other contaminants so that these materials do not in the next detection cycle promote trapping of $NO_x$ or other compounds which might interfere with selective detection of explosives vapors. At the remaining three stations the preconcentrator is cooled down in preparation for the next detection cycle. One or both of stations 6 and 7 may be unnecessary if sufficient cooling can be achieved without them.

As indicated above, the preconcentrator 24 or group of identical preconcentrators 24 carried by the carousel 30 function to collect and concentrate explosives vapors from air samples directed therethrough and then to release the collected vapors for analysis. For this purpose the preconcentrators contain a vapor-trapping structure formed of or coated with platinum, which has been determined to be a preferred material for collection and release of explosives vapors in a manner to avoid interferents such as nitrogen oxides ($NO_x$) typically present in air samples. Other metals in the platinum metals group, such as rhodium, palladium, and iridium; and alloys of these metals may also be suitable for use as the explosives vapor trapping medium in the preconcentrators.

Figure 4:
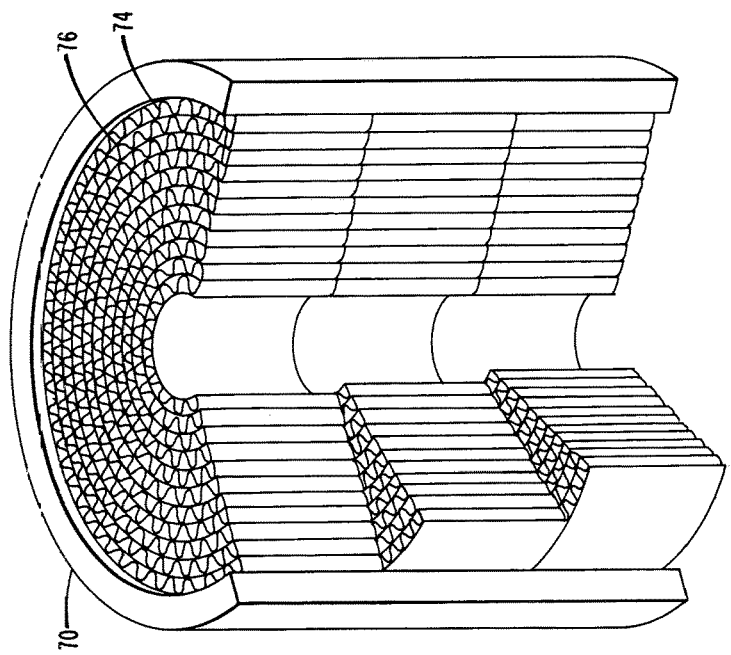
FIG. 4 is a perspective view, with portions removed to illustrate internal details, of a sample preconcentrator with multiple collector layers in series.
Figure 3:
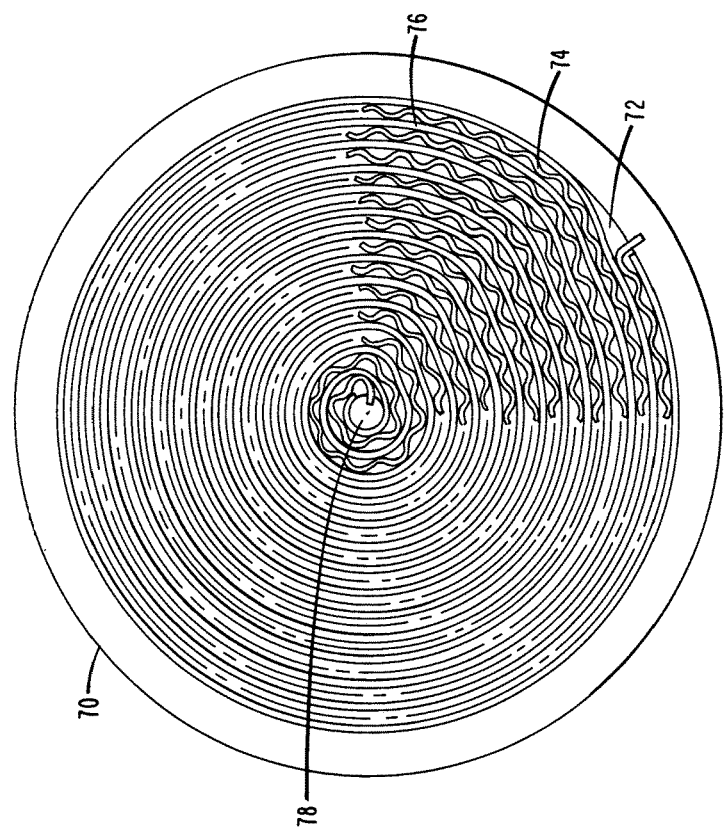
FIG. 3 is an end view of a preconcentrator for use in the detector of FIG. 1 and showing details of its spiral windings and various electrical connections.

A preferred preconcentrator 24 for use in the detector 20 of the invention, as illustrated in FIGS. 3 and 4, comprises an open-ended cylindrical metal housing 70 or cartridge containing a collector 72 shaped to expose a large surface area and provide a low-pressure drop to gaseous samples flowing through the preconcentrator. The compact cylindrical design of the preconcentrator provides a relatively small wall area, which helps minimize the loss of explosives vapors due to sorption of sample vapors by the inner wall of the housing 70, and the inner wall preferably is lined or coated with a material such as mica to which explosives vapors and $NO_x$ do not readily adhere. The vapor-sorbing portion of the collector 42 is a thin, corrugated ribbon 74 of platinum or a metal electroplated with platinum and wound into a tight spiral. This preconcentrator ribbon 74 is sandwiched between layers of an insulator strip 76 formed of a material such as mica which substantially neither adsorbs nor releases explosives vapors. As best shown in FIG. 3, the insulator strip 76 is also wound into a tight spiral so that the collector 72 formed by the combination of ribbon and insulator strip is a honeycomb-like structure offering a tortuous flowpath with numerous nearly triangular openings. The tortuous nature of the flowpath may be increased without substantially increasing the pressure drop by providing multiple collector layers in series such as is shown in the three-layer structure of FIG. 4.

The ribbon 74, in addition to trapping explosives vapors when samples are drawn through the preconcentrator 24, also serves as an electrical conductor so that, following collection of vapors, the ribbon 74 may be flash-heated to release the concentrated sample vapors into a stream of inert carrier gas for flow to the pyrolyzer 25. For this purpose one end of the ribbon 74 is, as shown in FIG. 3, connected to an electrically conductive pin 78 mounted in the center of the preconcentrator 24. The pin 78, which also provides support for the collector structure 72, is in turn connected to a variable high-current, low voltage power supply 42 (FIG. 1.). The other end of the ribbon 74 is attached to the housing 70, which serves as a second electrode for the ribbon 74 and in turn is connected through a preconcentrator holder (to be described hereinafter) to the power supply 42. Because the ribbon 74 has low thermal mass, it can be heated and cooled quickly, facilitating rapid release of sample vapors and fast cleaning of the preconcentrator 24.

To facilitate rapid collection and analysis of multiple samples, as in a detection system employed to screen persons entering a restricted area, several preconcentrators 24 of the above-described type are held in a carousel such as the carousel 30 illustrated in FIG. 5. The carousel 30 comprises three main parts: a front face plate 86, a rear housing 88, and a rotatable preconcentrator holder 90 supported between the housing 88 and the plate 86. The rotatable preconcentrator holder 90 and the front face plate 86 fit within the rear housing 88, with the front face plate 86 being fixed in position by guard tabs 92 on the outer periphery of the plate 86 which fit tightly in slots 94 of the rear housing 88. Thus only the preconcentrator holder 90 is free to rotate—e.g., by means of a motor (not shown) connected to a central shaft 96 extending through the holder 90. Rotation of the holder 90 positions each of the seven preconcentrators 24, in turn, at each of seven stations at which steps relating to explosives vapors detection are performed during a detection cycle, and electrical input to each preconcentrator 24 is provided through the electrical connections 80 in the holder 90.

Also shown in FIG. 5 are portions of the various flow lines connected to the rear housing 88 and to the front face plate 86 of the carousel 30. For example, note the flow line 32 which, as illustrated in FIG. 1, leads from the carousel 30 at station 1 to the suction fan 34 used to draw samples into the preconcentrators 24. The line 32 may, as shown in FIG. 5, have a cone-shaped connection 100 between a large diameter flow line section 102 sized to accommodate a fan of moderate flow rate capacity (e.g., between about 30-70 liters per minute) and a flow line section 104 having a diameter similar to that of the housing 70 of each preconcentrator (e.g., a diameter of about 0.6 centimeters). The line 32 is followed, in counterclockwise arrangement as viewed in FIG. 5; by the outlet line 41 through which a preconcentrator 24 is evacuated, then the flow line 44 which leads to the pyrolyzer 25, and finally by a single outlet line 104 connected between the purge pump 48 and a manifold 106 of the rear housing 88 which collects cleanup and cooldown gases from stations 4-7.

As shown in FIG. 1 the preconcentrator 24 at station 3 communicates by the interface 44 to a pyrolyzer 25 which is connected to an NO analyzer 26. The NO analyzer 26 may be a detector utilizing chemiluminescence, photoionization, electron capture, or any other technique capable of rapid detection of low levels of NO gas.

A preferred analyzer 26 is a modified version of a TEA Analyzer, Model 543, available from Thermedics Inc., 470 Wildwood Street, Woburn, Mass. The TEA analyzer includes a pyrolyzer, and thus although for purposes of generality the analyzer 26 of FIG. 1 is indicated as separate from the pyrolyzer 25 shown therein, in discussion hereinafter of the TEA analyzer it should be understood that the pyrolyzer 25 is incorporated into and forms part of the analyzer 26.

The main principle of operation of the TEA analyzer is to thermally decompose compounds containing nitro ($-NO_2$) or nitroso ($-NO$) functional group so as to selectively liberate nitric oxide (NO) gas and then to measure the nitric oxide liberated by reacting the nitric oxide with ozone and measuring the chemiluminescent emission resulting from the reaction. A more detailed explanation of the construction and operating principles of this line of analyzers is given in U.S. Pat. Nos. 3,973,910 and 3,996,003, and the disclosures of these patents are incorporated herein by this reference to them.

As illustrated in FIG. 1, the pyrolyzer 25 is operable to receive explosives vapors from a preconcentrator 24 at station 3 along the flow line or interface 44. Preferably the line 44 comprises a gas tube of relatively wide bore which is as short as possible and is heated—e.g., to a temperature in the range of about 200° C.-300° C., to minimize loss or degradation of the flash-heated vapors flowing along the line 44. A preferred pyrolyzer 25 is an electrically-heated cylindrical tube with a non-oxidizing inner wall surface—e.g. formed of a material such as quartz. During operation the pyrolyzer 25 is maintained at a temperature in the range of about 350° C.-1000° C., preferably about 800° C., so as to thermally decompose explosives vapors received in fragmented or partially-fragmented form from the preconcentrator 24 and to split off NO gas from these vapors. For most explosives a pyrolyzer temperature of about 650° C. is suitable; however, some explosives such as TNT require a higher temperature for complete decomposition into NO gas and other products.

To remove contaminants and pyrolyzer decomposition products whose presence could interefere or compete for detection with NO gas, the outlet end of the pyrolyzer 25 is connected to either a cold trap (not shown) or; preferably, to a cartridge trap 116 containing a solid sorbent such as granular molecular sieve material. The construction and operation of a suitable cartridge trap is set forth in U.S. Pat. No. 4,301,114, whose disclosure is incorporated herein by this reference thereto.

The pyrolyzer decomposition products which pass through the cartridge trap 116 flow to a chemiluminescent reaction chamber 120 which is also supplied through a line 122 with ozone from an ozonator 124. In the chamber 120 nitric oxide gas present in the decomposition products reacts rapidly with ozone, giving off chemiluminescent light in a narrow wavelength range (e.g., 0.6-2.8 microns). A photon detector 126 adjacent to the reaction chamber 120 is operable to detect the chemiluminescent light and together with the microprocessor 27 yields signals (including an alarm) indicating the presence of explosives.

Calibration of the detector 30 may be readily accomplished by one or a combination of techniques. To check operation of the analyzer 20, gas from a tank 134 (FIG. 1) containing a known amount of NO mixed with nitrogen gas may be introduced into the pyrolyzer 25 along a line 136 connected to the interface 44. Detector response can be verified by generating vapors from various explosives by flowing air over a sample of the explosive, then introducing these vapors into the detector. Alternatively, the detector operation can be checked on an explosive compound of interest or a harmless surrogate compound by positioning the compound in a test chamber communicating with the explosives detector (e.g. having a technician carry the compound in transport through the test chamber, and sweeping air through the test chamber and into the detector for processing).

Operation of the detector 20 will now be reviewed with reference to FIGS. 1 and 2. Air which may contain explosives vapors is first drawn through a preconcentrator 24 at station 1, with pressure of the preconcentrator remaining at close to atmospheric and its temperature being close to ambient (e.g. 25° C.). At station 2 the preconcentrator is evacuated while being heated to a temperature of about 150° C., with pressure rapidly decreasing to about 5 torr Pressure within the preconcentrator falls to about 0.2 torr during continued evacuation at station 3, then about halfway through operations at station 3, the preconcentrator ribbon 74 is flash-heated, increasing its surface temperature in a few seconds or less to about 800° C. This surge in temperature vaporizes and at least partially decomposes the labile organic compounds on the platinum surface of the ribbon 74. These compounds and decomposition fragments are directed into the pyrolyzer 25 where thermal decomposition into NO gas and other products is completed. If explosives vapors were present in the air sample passed through station 1, subsequent detection of the NO gas in the analyzer 25 then produces a single peak on the signal output of the analyzer 26. After the measuring process has been completed, the preconcentrator, now at station 4, has its ribbon surface again heated to about 800° C. in the presence of air at atmospheric pressure to clean the ribbon surface. The temperature of the preconcentrator then falls gradually during cooldown with air at stations 5, 6, and 7 so that the preconcentrator is again ready for sampling when re-positioned at station 1.

Figure 6:
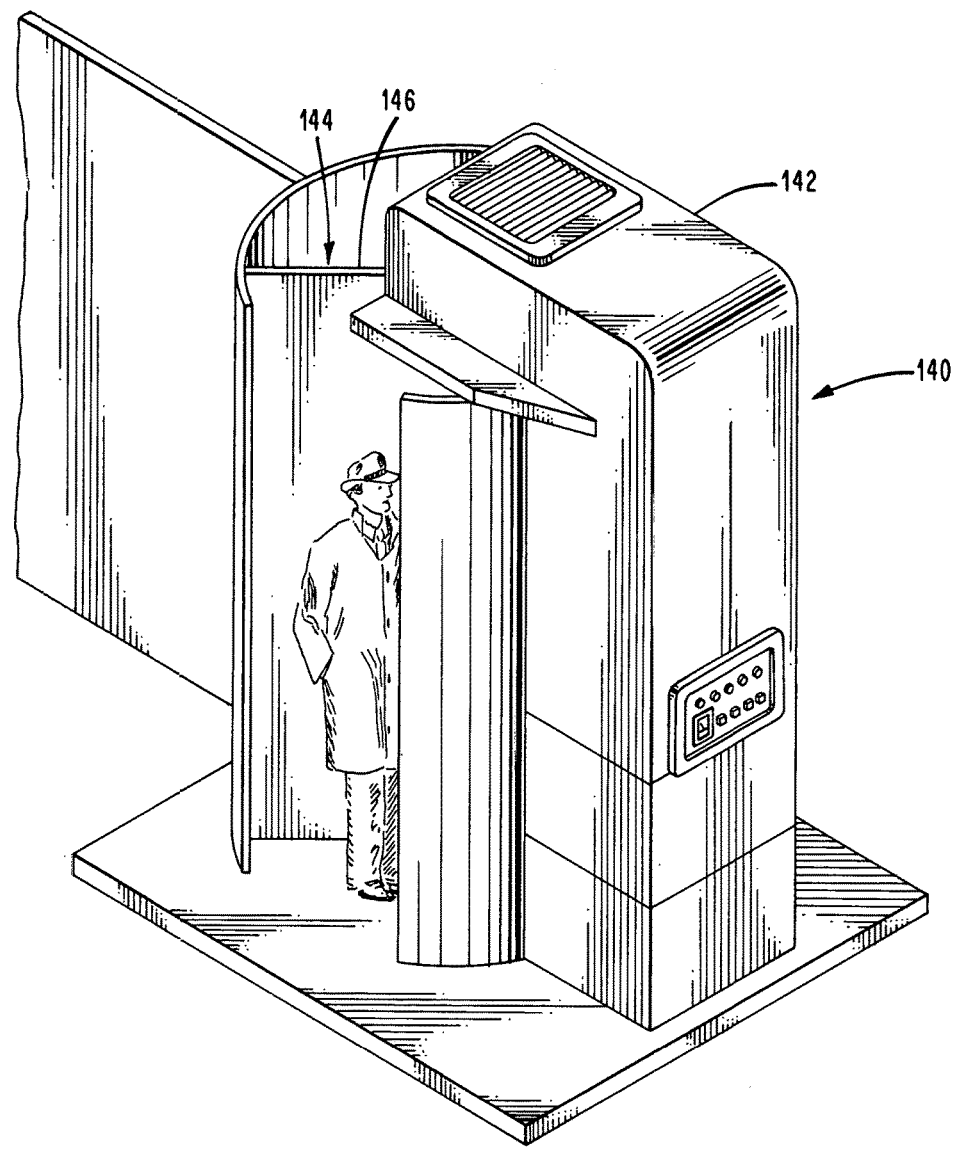
FIG. 6 is a view in perspective of a walk-through detection system employing the explosives vapor detector of FIG. 1.
Figure 7:
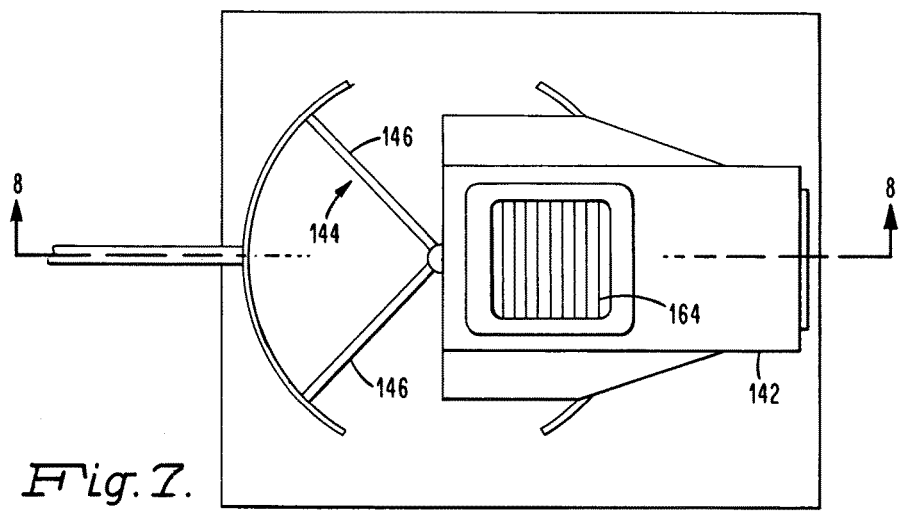
FIG. 7 is a top view of the walk-through system of FIG. 6.
Figure 8:
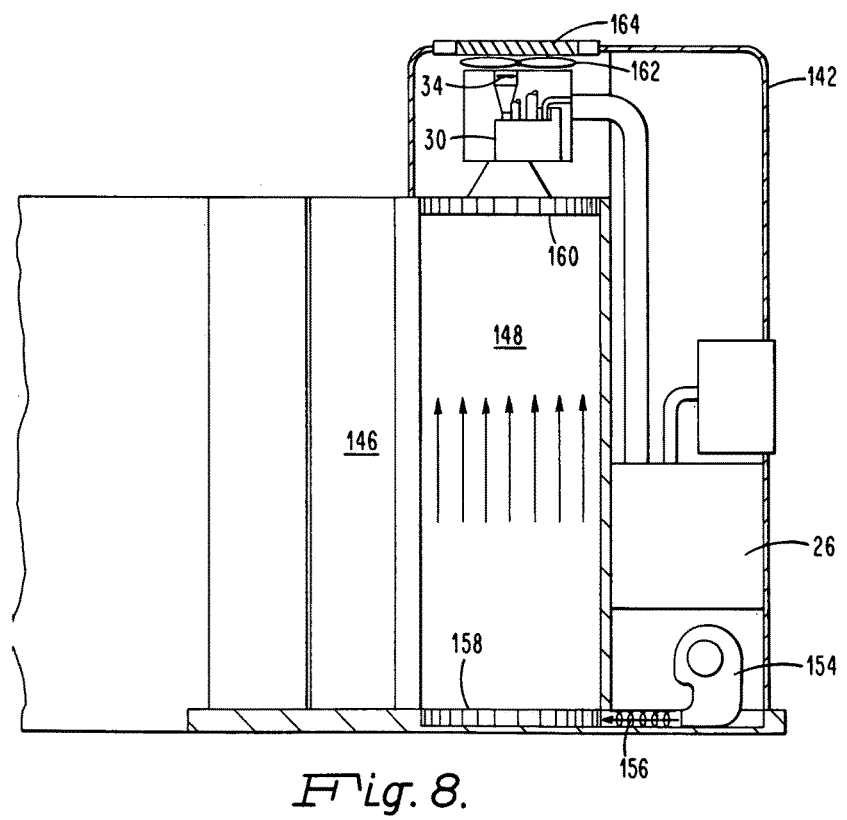
FIG. 8 is a side view of the walk-through system taken along the line 8-8 of FIG. 7.

A preferred system in which the detector 20 may be incorporated is illustrated in FIGS. 6-8. The walk-through explosives vapor detection system 140 includes a housing 142, a revolving door 144 with four door sections 146 mounted within the space defined by the housing 142, and a detector 20 which collects and analyzes air samples acquired from persons who pass one at a time through the system. To permit screening of persons, the system 140 includes a test chamber 148 formed as a completely enclosed space between the housing 142 and any two of the door sections 146 when such sections move to the quadrant of the housing in which the detector 20 is mounted. As shown in FIG. 8, air samples to be processed in the detector 20 are acquired from heated air flowing generally upwards through the test chamber 148. The air flow is provided by an air blower 154 which directs air over an air heater 156 and through a flow straightener 158 adjacent to the bottom of the test chamber 148. In its passage through the test chamber 148 the heated air picks up explosives vapors, if explosives are present on, or are carried by; the person being screened. This heated air is drawn upward out of the test chamber 148 through a flow straightener 160 by two fans in the top portion of the housing 142. One, a large fan 162, provides upward air velocity and exhausts air through louvres 164 in the top of the housing 142. A smaller fan 34 in flow line 32 of the detector 20 draws about ten percent of the air (20-40 percent of that which has passed over the person being screened) through a preconcentrator in a carousel 30 of the detector 20. This air sample, minus the explosives vapors trapped in the preconcentrator, then flows out through the exhaust louvres 164. The trapped explosives vapors are subsequently released, then passed to and detected by; the vapor analyzer 26 (including a pyrolyzer) which is positioned within the housing as close as practicable to the carousel 30 so as to minimize sample loss and the time required for analysis.

As described earlier in connection with FIGS. 1 and 5, the carousel 30 may rotate to cycle its preconcentrators among the various processing stations of the detector 20. Alternatively, the test chamber 148 and various flow lines of the detector may rotate about a fixed carousel. In either case sampling of a person in the test chamber 148 can be completed in about six seconds so that up to ten persons per minute can be processed through the walk-through detection system. Analysis of collected samples is completed in about twelve additional seconds, with a preconcentrator moving, or flow lines moving relative to it, to two more stations. Shorter sampling and analysis periods can be achieved if less sensitivity is required than the 1 part in $10^{14}$ or better considered achievable by the explosive vapors detector 20 of the invention.

The sample analyzer 26 may, as previously disclosed with reference to FIG. 1, comprise a chemiluminescent NO analyzer commercially available as a TEA Analyzer Model 543 from Thermedics Inc., but modified to improve sampling speed and sensitivity as desired in analysis of explosives vapors. These modifications include providing a large capacity, high speed vacuum pump and wide bore gas flow lines. Also, the volume of the chemiluminescent reaction chamber 120 is increased in proportion to the decreased pressure due to the higher speed vacuum pumping, and the inside surface of the chamber 120 may be polished and gold plated to improve reflectivity. To further improve sensitivity of the analyzer 26, the amplifier of the photon detector tube used in detecting chemiluminescent light is modified to utilize photon counting instead of direct amplification of current.

Figure 9:
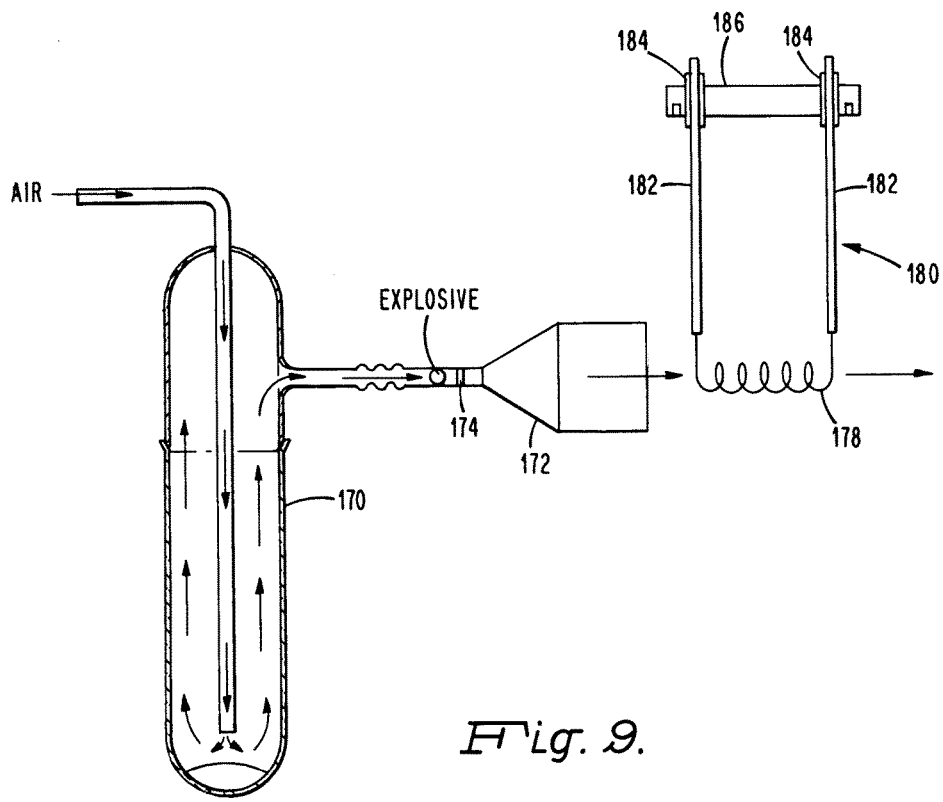
FIGS. 9 and 10 are schematic diagrams of portions of an experimental detector used to demonstrate the sensitivity and particularly the selectivity of detection of the invention.

To demonstrate the high selectivity and high sensitivity of the detector of the invention, a test apparatus was constructed and the detection techniques of the invention were applied to small amounts of vapors of various known compounds. These compounds included explosives and compounds which if also present might compete for detection with explosives. The test apparatus, shown in FIGS. 9 and 10, included four major components: a vapor generator, a preconcentrator, an evacuation/flash-heating chamber, and a chemiluminescence detector. The vapor generator (FIG. 9) comprised a glass impinger 170 attached to a glass funnel 172, with vapors of explosives compounds being generated by flowing air at a flow rate of about 12 liters/minute through the impinger 170 and over a sample of the compound of interest held in place behind a stainless steel screen 174 in the narrow neck of the funnel 172. These vapors were passed over a coil of platinum wire 178 forming the vapor-trapping portion of a preconcentrator 180. The 0.010 inch-diameter wire 178, about three feet in length, was spot-welded across two thicker platinum rods 182 which in turn were attached to copper-ceramic feedthroughs 134 welded to a stainless steel plate 186. All exposed surfaces of copper and stainless steel were covered with vacuum grease to prevent the metals from degassing when the preconcentrator 180 was subject to vacuum and flash-heating. A variable, high current, low-voltage power supply (not shown) was connected across the platinum rods 182 to provide power to flash-heat the wire 178 of the preconcentrator 180 for releasing trapped vapors into the evacuation/flash-heating chamber (FIG. 10).

Figure 10:
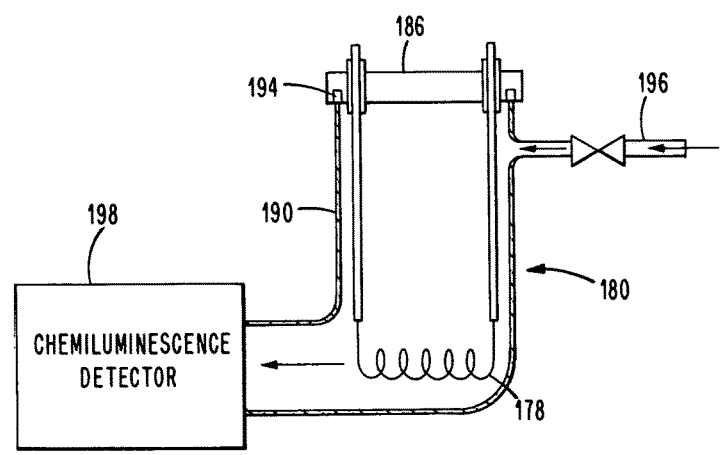

FIG. 10 shows the preconcentrator 180 installed in a glass evacuation/flash-heating chamber 190, a vacuum tight seal being provided between the stainless steel plate 186 of the preconcentrator 180 and the top of the chamber 190 by means of a rubber gasket 194. A gas line 196 connected to a supply of commercial grade nitrogen gas (not shown) communicated with the interior of the chamber 190 to sweep gases from the chamber 190 into a chemiluminescence detector 198 (TEA Analyzer Model 543 modified to contain a larger capacity vacuum pump and quarter-inch O.D. Teflon tubing internally instead of the normal eighth-inch size). Heating tape (not shown) was wrapped around the outside surface of the chamber 190 for "baking out" the chamber 190 and for maintaining the preconcentrator wire 178 at a temperature in the range of about 100° C.-220° C. during degassing and prior to flash-heating.

Before being used to evaluate samples, the test apparatus was calibrated by determining its response to injection of a known amount of NO gas into the nitrogen carrier gas stream of gas line 196. Based on the assumption that the minimum detectable response was three times the peak-to-peak noise of the TEA analyzer 154 the response to NO gas indicated a sensitivity corresponding to $20\times10^{-12}$ grams of RDX explosive. If the preconcentrator 140 were 100% efficient in collecting vapors, the test apparatus in the form utilized (i.e., without sensitivity enhancements achieved by modifying the TEA analyzer) would have a sensitivity of about one part in $10^{14}$ on an air sample of 400 liters.

After the test apparatus was calibrated, various compounds representing possible sources of interference with detection of explosives vapors were evaluated for possible response. For example, since typical air samples contain nitrogen oxides ($NO_x$ as NO and $NO_2$) at levels of 0.1-1.0 ppm (thus as much as $10^8$ times the concentration of explosives whose monitoring is desired) it was important to demonstrably eliminate $NO_x$ as a potential interferent. The features of explosives vapor detection of the invention which in fact did eliminate $NO_x$ as an interferent are (1) use of a collector surface (e.g. platinum) which traps explosives vapors but does not trap significant quantities of $NO_x$, and does not tightly hold the $NO_x$ which in fact gets trapped; (2) use of silicone grease to cover other metal surfaces in the detector which could absorb $NO_x$; (3) heating of the collector surface prior to use to burn off contaminants which could adsorb $NO_x$; and (3) moderate heating and degassing of the collector surface (prior to flash-heating to drive off explosive vapors) to remove gases from the air space of the preconcentrator as well as any entrapped $NO_x$. With these features utilized in the test apparatus and its operation, the peak height response of the apparatus following exposure of the preconcentrator to 12, 60, and 80 liters of air was minimal and indicated virtual elimination of $NO_x$ as a possible interferent in explosives vapors detection.

Table 2 lists several other compounds and substances evaluated for possible response on the test apparatus. It indicates that none of the commonly-encountered solvents such as dichloromethane, acetone; methanol, and toluene gave a response, nor did the commercial perfumes tested. Since those perfumes contain synthetic di- and/or tri-nitrobenzene compounds, which are similar in structure to TNT, the absence of a response to them is indicative of the extraordinary selectivity of the detection method and apparatus of the invention.

TABLE 2

SUBSTANCES TESTED FOR INTERFERENCE

| COMPOUND | INTERFERENCE |
| --- | --- |
| Air | None |
| Methanol | None |
| Ethanol | None |
| Toluene | None |
| Dichloromethane | None |
| Acetone | None |
| Ethyl Acetate | None |
| Hexane | None |
| Masking Tape and Glue | None |
| Soap Solution | None |
| Plastic Bags | None |
| Plastic Coca Cola Bottles | None |
| PVC | None |
| "Skin Bracer" (Mennon) | None |
| "Wild Musk" Perfume (Coty) | None |
| Nitromethane | None |
| Clothing, Various | None |
| Nitrobenzene | 400 units |
| Tobacco Smoke | 200 units |

The only two substances listed in Table 2 to give measurable, though small, responses were cigarette smoke and nitrobenzene. (By comparison to the 200 unit response of cigarette smoke, the explosive C4 when tested gave a response of greater than 12000 units as indicated in Table 3 referred to hereinafter.) Since the cigarette smoke test was conducted by passing a smoke plume directly over the platinum surface of the preconcentrator for twenty seconds—i.e., using a level of tobacco smoke far higher than would likely be encountered in an airport or other screening area, it is unlikely that ambient levels of tobacco smoke will interfere with detection of explosives vapors. The response to a five-minute (60 liters of air) exposure to nitrobenzene, though measurable, was still fairly small.

Figure 12:
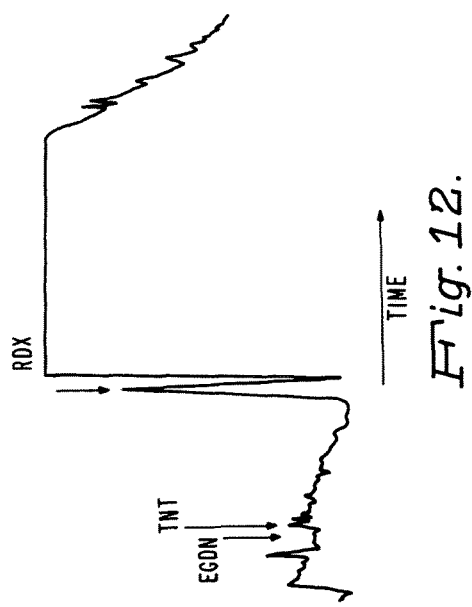
FIGS. 12 and 13 are chromatographs of samples of RDX crystals analyzed by a high pressure liquid chromatograph interfaced to a chemiluminescence NO analyzer.
Figure 13:
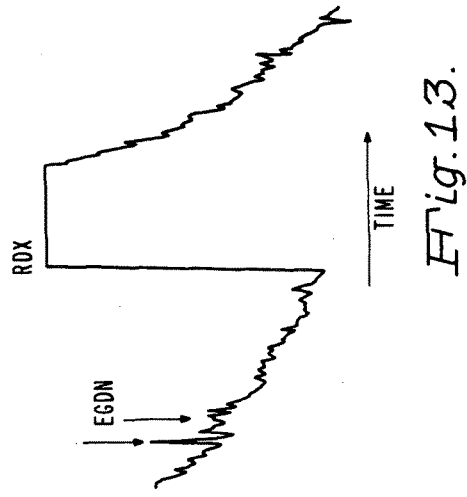
Figure 11:
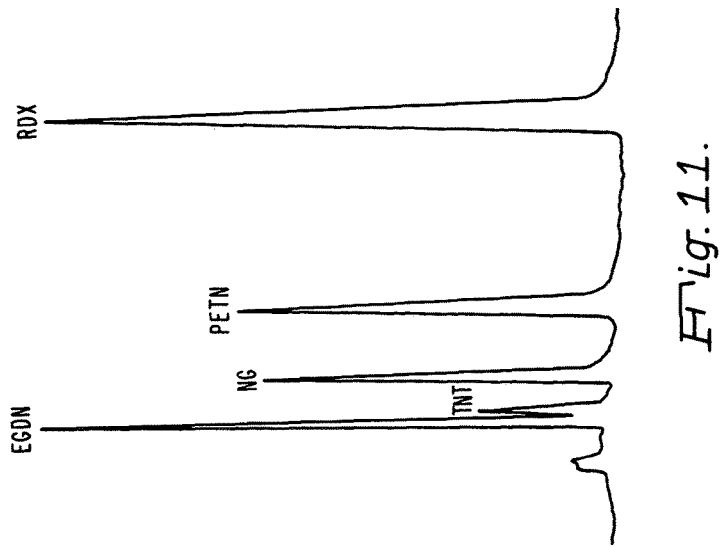
FIG. 11 is a chromatogram of a standard solution of explosives analyzed by a high pressure liquid chromatograph interfaced to a chemiluminescence NO analyzer.

A major limitation of previous work on detection of vapors from samples of explosive compositions has been contamination of the test samples with traces of EGDN and other potentially interfering compounds. Thus prior to testing samples of explosives in the test apparatus shown in FIGS. 9 and 10, chemical analysis at the trace level were performed on each sample in a gas chromatograph (GC) or high pressure liquid chromatograph (HPLC) interfaced to a chemiluminescence NO analyzer (TEA analyzer) similar to that utilized in the test apparatus. FIG. 11 is a timewise signal trace (chromatogram) obtained from analysis in an HPLC/TEA analyzer combination of a standard solution containing the explosives EGDN, TNT, RG, PETN, and RDX. The chromatogram clearly shows a peak for each explosive. FIGS. 12 and 13 are chromatograms of similar analysis of two samples of RDX crystals from different sources. Both samples are free of EGDN, NG, PETN, and DNT, but the FIG. 12 sample is seen to have a small contaminant eluting just prior to the parent (RDX) peak. Accordingly, this contaminated sample and any others shown to be contaminated were not included in reported sample evaluations with the breadboard apparatus of FIGS. 9 and 10.

Explosives samples proven to be uncontaminated were tested in the above-described breadboard apparatus according to the following protocol: (1) the platinum wire 178 of the preconcentrator 180 was heated in air to red heat (about 800° C.) to burn off any carbonaceous material and contaminants; (2) the wire 178 was positioned in the airstream emerging from the funnel 172 of the explosives vapor generator and air was allowed to sweep over a sample in the funnel 172 for five minutes at a flow rate of twelve liters/minute. (Prior to each new analysis the vapor generator was cleaned and a zero data point obtained to demonstrate that the apparatus was indeed clean.) Temperature of the explosives sample was maintained at about 20° C. (except some water gel samples were collected with the vapor generator heated to about 40° C.); (3) the preconcentrator 180 was attached to the evacuation/flash-heating chamber 190 with the wire 178 extending into the chamber 190 and the wire 178 was heated to about 150° C. and degassed for 10-15 seconds; (4) the wire 178 was flash-heated to red heat under vacuum and with nitrogen carrier gas flowing, driving adsorbed vapors off the wire and into the TEA analyzer 198; and (5) the preconcentrator 180 was removed from the chamber 190 to prepare for repetition of steps (1) through (4) (each sample was tested at least four times).

FIGS. 14-17 show timewise signal traces of the output of the breadboard test apparatus resulting from tests conducted on samples of, respectively, crystalline RDX, C4, TNT, and ammonium nitrate using the above-described protocol. Each figure illustrates the response of the apparatus to 60 liters of air, followed by its response to 60 liters of air swept over a sample of the selected explosive. The downward pointing arrows above the signal traces indicate the times at which the platinum wire 178 of the preconcentrator 180 was reheated to ensure that no contaminants or explosive vapors remained on the wire.

The signals of FIGS. 14-17 show essentially zero response of the test apparatus to an air sample, but peak responses (at various attenuations of the TEA detector 198) to vapors of the explosives being tested. FIG. 17 and similar data on other water gels indicates that full scale response to ammonium nitrate is obtained when the sample is heated to body temperature (about 40° C.).

The results illustrated in FIGS. 14-17 and data from tests conducted on other explosives samples is summarized in Table 3. Those data indicate that the breadboard test apparatus readily detected all explosives tested. The test apparatus also demonstrated a sensitivity of about 1 part in $10^{11}$ even though its TEA analyzer was in order to boost selectivity, detuned in sensitivity by a factor of ten from commercially available TEA analyzer. With the earlier-

TABLE 3

SUMMARY OF EXPLOSIVE VAPOR TEST DATA

| Material | TEA Detector Attenuation | Signal Response (Peak Height Units) |
|---|---|---|
| Dynamite | 2048 | Overload |
| Ammonium Nitrate | 8 | 800 |
| Hercules Powergel | 2 | 100 |
| RDX, Recrystallized | 64 | >6,400 |
| C4 | 128 | >>12,800 |
| C4 | 128 | >12,800 |
| TNT, Demolition Block | 32 | >3,200 |
| TNT, Military | 64 | >>6,400 |
| TNT, Prills | 2048 | Overload |
| PETN, Primacord | 128 | >>12,800 | described modifications to the TEA analyzer, including increasing the size of its chemiluminescent reaction chamber and utilizing photon counting, this factor of ten in sensitivity can be regained and surpassed. Moreover, because air does not affect the background response of the detector, its sensitivity can be further boosted by increasing the volume of sample drawn through the detector. The lower detection limit of the explosives vapor detector of the invention, under real conditions, may be as low as several parts in $10^{16.}$ The explosives vapor detector of the invention may readily be utilized in systems other than the above-described walk-through explosives vapor detection system. For example, a vehicle "sniffer" for inspecting vehicles passing a checkpoint may include one or more flexible hoses each having a preconcentrator as described herein positioned at a sampling or probe end and having its opposite end connected to a fixed pyrolyzer, NO detector, and microprocessor. The probes could then be used to quickly and easily sniff various parts of a vehicle such as the trunk, engine compartment, and under portions, thus eliminating slow physical (manual) searches. Also, the explosives vapor detector can readily be incorporated into an air monitoring system of a building—e.g., as an ultrasensitive instrument which continuously sniffs the air-handling system of a building and accumulates a sample over a relatively long period of time (for example, 10-30 minutes) to determine whether explosives are present in the building. Still another system is a lightweight, portable version of the explosives vapor detector powered by rechargeable batteries. The inherently lower sensitivity of a portable detector relative to an electrically-powered, fixed version does not limit utility of the portable detector since it typically is used primarily to search at relatively close quarters—e.g., packages, envelopes and rooms. Also, its sensitivity can be boosted by increasing its sniffing time.

The invention may be embodied in other specific forms without departing from its spirit or essential characteristics. The present embodiments are therefore to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. Apparatus for selectively detecting, essentially in real time, vapors from explosives present in an air sample at low concentrations comprising:
    preconcentration means for collecting explosives vapors from said air sample, said preconcentration means including an open-ended cartridge containing (a) an electrically-conductive multi-layer collector having a surface effective to trap explosives vapors from said air sample while avoiding the trapping, in any substantial amount, of nitrogen oxides present in the air sample, said collector further being operable to release the explosives vapors and decomposition products thereof upon being flash-heated, and (b) insulating means for providing insulation between, and for supporting adjacent layers of, said collector, said insulating means being formed of a material which substantially neither traps nor readily releases nitrogen oxides;
    means for directing said air sample through said preconcentration means;
    means for evacuating said preconcentration means to remove gases therefrom substantially without removing trapped explosives vapors;
    means for flash-heating said collector to release explosives vapors therefrom and to thermally fracture and decompose said explosives vapors to selectively liberate nitric oxide gas; and
    a nitric oxide detector operable to detect nitric oxide gas liberated in said preconcentration means.

2. Apparatus as in claim 1 including a pyrolyzer connected between said preconcentration means and said nitric oxide detector, said pyrolyzer operable to selectively liberate nitric oxide gas from any explosives vapors whose thermal fracture and decomposition to produce nitric oxide gas was not completed in said preconcentration means.

3. Apparatus as in claim 1 wherein said collector comprises a ribbon formed into a spiral and having a surface of a material selected from the group consisting of platinum, rhodium, palladium, iridium, and alloys thereof, said means for flash heating said collector comprises a low voltage, high current power supply electrically connectable to said collector, and said preconcentration means includes an electrically conductive pin centrally disposed in said cartridge and electrically connectable to said power supply, one end of said ribbon being electrically connected to said pin and the opposite end of said ribbon being attached to said cartridge.

4. A method of selectively detecting vapors from explosives, said vapors being present in an air sample at low concentrations, and wherein said air sample contains nitrogen oxides as potential sources of interference with the detection of said explosives vapors at levels which may be substantially in excess of the concentration of said explosives vapors, comprising the steps in the order given of:

(a) directing said air sample through a cartridge containing a preconcentrator effective to trap explosives vapors from the sample while avoiding trapping of substantial amounts of nitrogen oxides or other contaminants in the sample whose subsequent release from the preconcentrator with said explosives vapors could interfere with analysis of the explosives vapors;

(b) evacuating from said cartridge air and contaminants trapped in the cartridge by heating said preconcentrator to a temperature in the range of about 25° C.-200° C. and applying a vacuum to, and flowing an inert gas through, the cartridge;

(c) flash-heating the preconcentrator to a temperature in the range of about 600° C.-900° C. to desorb the explosives vapors from said preconcentrator and to thermally fracture and decompose said explosives vapors to selectively liberate nitric oxide gas; and (d) detecting the liberated nitric oxide gas.

5. A method as in claim 4 including, between said flash-heating step and said nitric oxide detection step, pyrolyzing the products received from said preconcentrator to selectively liberate nitric oxide gas from any explosives vapors whose thermal fracture and decomposition to produce nitric oxide gas was not completed in said flash-heating step.

6. A method of screening persons one-by-one for possession of explosives, essentially in real time, comprising the steps in the order given of:

(a) providing a carousel containing an array of equally-spaced preconcentrator cartridges each having a preconcentrator effective to trap explosives vapors present in an air sample without trapping substantial amounts of nitrogen oxides;

(b) positioning the next person to be screened in a test chamber and removing from said chamber any person therein already screened;

(c) directing airflow over the person in said test chamber to form an air sample which may contain explosives vapors and, in addition, nitrogen oxides as Potential sources of interference with the detection of said explosives vapors at levels in excess of the concentration of said explosives vapors in the air sample;

(d) passing at least a portion of said sample through a clean cartridge of said array to trap explosives vapors therein;

(e) rotating said carousel and said test chamber relative to each other to place a clean cartridge of said array in fluid communication with said test chamber, and repeating step (b);

(f) while repeating step (c), evacuating air and contaminants from the cartridge which may have explosives vapors trapped therein from the person most recently screened in the test chamber;

(g) repeating step (g);

(h) while repeating step (f), flash-heating the preconcentrator of said evacuated cartridge to a temperature in the range of about 600° C.-900° C. to desorb explosives vapors therefrom, pyrolyzing said desorbed vapors to selectively liberate nitric oxide gas, and detecting said liberated nitric oxide gas;

(i) repeating step (e);

(j) while repeating step (h), reheating the preconcentrator of said flash-heated cartridge to a temperature in the range of 600° C.-900° C. to clean said preconcentrator;

(k) repeating step (e); and (e) while repeating step (j), directing air through said reheated cartridge to cool said preconcentrator.

7. A method as in claim 4, wherein said explosives vapors are present in, and detected from, said air sample at concentrations of one part in $10^{14}$ or less.

8. A method as in claim 4 wherein said step of detecting the liberated nitric oxide gas comprises reacting said nitric oxide gas with ozone and detecting the chemiluminescent radiation emitted at selected wavelengths by said reaction.

9. A method as in claim 8 wherein said steps (a) through (d) are performed in a total time interval of less than thirty seconds.

10. A method as in claim 7 wherein said air sample contains nitrogen oxides as potential sources of interference with the detection of said explosives vapors at levels in the range of between about one part in $10^6$ and one part in $10^7$.

* * * * *